(12) United States Patent  
Samsonova

(10) Patent No.: US 9,725,711 B2
(45) Date of Patent: Aug. 8, 2017

(54) METHOD AND DEVICE FOR SELECTIVE HYPERTHERMIC DAMAGE OF TARGET CELLS

(71) Applicant: Natalia Samsonova, Chesterfield, MO (US)

(72) Inventor: Natalia Samsonova, Chesterfield, MO (US)

(73) Assignee: CellEraser, LLC, Chesterfield, MO (US)

( * ) Notice: Subject to any disclaimer, the term of this patent is extended or adjusted under 35 U.S.C. 154(b) by 60 days.

(21) Appl. No.: 14/639,093

(22) Filed: Mar. 4, 2015

(65) Prior Publication Data

US 2015/0252353 A1 Sep. 10, 2015

Related U.S. Application Data

(60) Provisional application No. 61/950,832, filed on Mar. 10, 2014.

(51) Int. Cl.
 C12M 1/00 (2006.01)
 C12N 13/00 (2006.01)

(52) U.S. Cl.
 CPC .................................... C12N 13/00 (2013.01)

(58) Field of Classification Search
 USPC ......... 435/173.4, 283.1; 250/341.1; 219/678; 600/10, 407
 See application file for complete search history.

(56) References Cited

U.S. PATENT DOCUMENTS

| | | | |
|---|---|---|---|
| 4,629,687 A | 12/1986 | Schindler et al. | |
| 4,873,995 A * | 10/1989 | Kikuchi | A61N 5/02 219/701 |
| 5,035,693 A | 7/1991 | Kratzer et al. | |
| 6,777,684 B1 * | 8/2004 | Volkov | G01N 21/3581 250/341.1 |
| 6,804,385 B2 * | 10/2004 | Eisfeld | G06K 9/00127 359/368 |
| 7,016,725 B2 * | 3/2006 | Palti | A61N 1/326 435/173.7 |
| 7,912,527 B2 * | 3/2011 | Robertson | A61B 5/01 250/339.04 |
| 8,401,263 B2 | 3/2013 | Palsson et al. | |
| 8,401,668 B2 * | 3/2013 | Deem | A61B 18/18 607/101 |
| 8,406,894 B2 * | 3/2013 | Johnson | A61N 5/04 606/33 |
| 8,747,398 B2 * | 6/2014 | Behnke | A61B 18/18 606/33 |
| 8,957,810 B2 * | 2/2015 | Babakhani | G01S 13/89 324/337 |
| 2008/0033422 A1 * | 2/2008 | Turner | A61B 18/18 606/33 |

* cited by examiner

Primary Examiner — Nina Bhat

(57) ABSTRACT

Device and method for selective hyperthermic damage of target cells by means of millimeter wave radiation. Cells in a culture medium are placed in a cell cultureware and millimeter wave radiation is delivered via a waveguide to a predetermined region of exposure of the culture medium. The device and method are safe and efficient for use in clinical and research applications.

8 Claims, 7 Drawing Sheets

METHOD AND DEVICE FOR SELECTIVE HYPERTHERMIC DAMAGE OF TARGET CELLS

CROSS-REFERENCE TO RELATED APPLICATIONS

This application is based on and claims priority to provisional U.S. patent application Ser. No. 61/950,832, which was filed on Mar. 10, 2014.

FIELD OF THE INVENTION

The present invention relates generally to systems and methods for selective hyperthermic damage of target cells within cells in a culture medium, and more specifically, to a method and device for selective hyperthermic damage of unwanted cells within a cell population with millimeter wave radiation.

BACKGROUND OF THE INVENTION

Known methods for targeted elimination of anchorage-dependent cells generally utilize laser technology such as laser ablation and laser microdissection. In these methods a high power laser beam (usually from a pulsed UV laser) is used to either sweep over the surface to lethally illuminate the unwanted cells, or to cut out the cells of interest and physically separate them from the remaining cells. The shortcoming of the laser ablation approach is that a lot of free radicals and products of oxidation are formed during the ablation process. These aggressive byproducts harm the desired cells. The microdissection approach is not sterile and requires special consumables. All laser-based methods need special and very expensive equipment, precise laser optics adjustment and in some cases, addition of special light energy absorbing dye to the cell media to intensify the cell damage. The majority of these methods cannot be used with standard microscopes and cannot be performed manually by an inexperienced operator.

As known in the art, direct use of radiation in the infrared area is not applicable for selective cell ablation, as this radiation is strongly absorbed by glass, plastic and water. Therefore, if an infrared beam would be applied to glass or plastic bottom of a cell cultureware containing cells in a culture medium, it would heat both the cultureware bottom and the medium in the cell cultureware and therefore could not be used for selective local ablation of the cells. Besides, the intense infrared radiation is dangerous for vision. Despite not being visible, infrared radiation can still pass through the anterior structures of the eye and reach the retina. Since human eyes are unable to detect infrared radiation, there would be no blink or aversion reflex to protect the eyes from the damage if the eyes are exposed to intense infrared radiation.

Thus, there exists a need for a safe method and device for selective hyperthermic damage of target cells, specifically for irreversible damage and ablation of target cells within a cell population, that overcome the limitations of previously known methods and devices.

A need also exists for a method and device for selective hyperthermic damage of target cells, which are efficient for use in clinical and research applications.

A need further exists for a method and device for selective hyperthermic damage of target cells which are capable of being implemented with any type of known standard microscopes and could be performed manually by an inexperienced operator.

SUMMARY OF THE INVENTION

As known in the art, millimeter wave radiation is used in a variety of applications, from voice and data transmission and high-resolution radar imaging to body scanning and body imaging.

The present method is based on water absorption of millimeter wave radiation that occurs in both cell medium and cell material. Generally, the method employs millimeter waves that have water penetration depth of about 0.4 mm (W-band from 75 to 110 GHz) or less (for F, D and G bands). The millimeter waves are guided to the cell cultureware via a special waveguide that provides a localized irradiation spot of a controllable size. Millimeter waves rapidly heat a narrow layer (about 0.4 mm or less) of a media volume comprising unwanted cells near an external surface of a cell cultureware (made from glass or thin plastic) to about 58-60° C. The cells locally heated by millimeter wave radiation even for a short time are irreversibly damaged, as mammalian cells in culture medium or in tissues do not survive if exposed to temperatures exceeding 48-50° C. even for a short time interval (less than 1 minute). According to survival data of mammalian cells at elevated temperatures, there are no surviving cells starting at about 48° C. even though the cells are heated for less than 30 seconds. Higher temperatures (about 58-60° C.) sharply shorten the critical exposure time required to kill the cells by heating to less than 2-3 seconds. Such a short time to achieve cell death at 58-60° C. is attributed to the fast and irreversible denaturation of cell proteins.

In accordance with the subject application, there is provided an improved method for selective hyperthermic damage of target cells, specifically for irreversible damage of target cells within a cell population, that overcome the limitations of previously known methods and devices.

Further, in accordance with the subject application, there is provided an improved device for selective hyperthermic damage of target cells, specifically for irreversible damage of target cells within a cell population, that overcome the limitations of previously known methods and devices.

Still further, in accordance with the subject application, there is provided a method and device for selective hyperthermic damage of target cells, which are efficient for use in clinical and research applications.

Yet further, in accordance with the subject application, there is provided a method and device for selective hyperthermic damage of target cell which are capable of being implemented with any type of known standard microscopes and could be performed manually by an inexperienced operator.

According to one aspect of the subject application, there is provided a method for selective hyperthermic damage of target cells. The method comprises the steps of providing a millimeter wave radiation; and delivering the millimeter wave radiation to a predetermined spot of an external surface of an associated cell cultureware having cells in a culture medium placed therein, via a waveguide, exposing thereby a predetermined region of exposure of the cells in the culture medium to the millimeter wave radiation. Radiation power and exposure time of the millimeter wave radiation, and positional relationship of the end face of the waveguide and of the target cells are selected such as to provide selective hyperthermic damage to the target cells in the predetermined region of exposure of the cells in the culture medium.

In an exemplary embodiment, the hyperthermic damage is irreversible.

In one embodiment, the predetermined region of exposure may be visualized with an infrared sensitive thermal vision camera. In another embodiment, the exposure time may be about 2-3 sec, wherein the target cells in the predetermined region of exposure may be heated to a temperature of about 58-60° C.

In another embodiment, the method may further comprise a step of visualizing the predetermined region of exposure with an infrared sensitive thermal vision camera.

In an exemplary embodiment, the exposure time is about 2-3 sec, wherein the target cells in the predetermined region of exposure are heated to a temperature of about 58-60° C.

In another exemplary embodiment, the method may further comprise a step of visualizing the target cells in the predetermined region of exposure via bright-field or fluorescence microscopy.

In another exemplary embodiment, the millimeter wave radiation is in a frequency band of 75 to 110 GHz.

In another embodiment, the predetermined region of exposure has a diameter in the range of from about 0.25 mm to about 1.3 mm.

In an exemplary embodiment, an end face of the waveguide is positioned below an associated cell cultureware having cells in a culture medium placed therein, in proximity of the predetermined spot, exposing thereby the predetermined region of exposure of the cells in the culture medium located above the predetermined spot, to the millimeter wave radiation.

According to another aspect of the subject application, there is provided a device for selective hyperthermic damage of target cells that comprises a source of millimeter wave radiation, and a waveguide adapted for delivering the millimeter wave radiation to a predetermined spot of an external surface of an associated cell cultureware having cells in a culture medium placed therein, to provide for exposing a predetermined region of exposure of the cells in the culture medium to the millimeter wave radiation. An end face of the waveguide is positioned in close proximity of the predetermined spot. Radiation power and exposure time of the millimeter wave radiation, and positional relationship of the waveguide end face and the target cells are selected such as to provide selective hyperthermic damage to the target cells in the predetermined region of exposure of the cells in the culture medium.

In one embodiment, the device may further comprise a visualizing module adapted for visualizing the cells in the culture medium placed in the associated cell cultureware. The visualizing module may comprise a microscope, wherein the associated cell cultureware having cells in the culture medium placed therein is positioned on a microscope stage. In one embodiment, the microscope may be motorized. In a specific embodiment, the microscope may be a fluorescent or a bright-field microscope.

In another embodiment, the microscope is an upright microscope, and wherein the end face of the waveguide is positioned below a bottom of an associated cell cultureware having cells in the culture medium placed therein, exposing thereby the predetermined region of exposure of the cells in the culture medium located above the predetermined spot, to the millimeter wave radiation. The waveguide may comprise a first portion positioned horizontally relative to the microscope stage and a second portion positioned upright relative to the microscope stage, wherein the second portion is connected with the first portion via a 90 degree E-plane waveguide bend.

In an exemplary embodiment, the visualizing module may further comprise at least one of: a long working distance objective, a CCD camera for image capture, an infra-red camera for visualization on a monitor and a motorized stage to hold and move the associated cell cultureware with the cells in the culture medium placed therein.

Still other objects and aspects of the present invention will become readily apparent to those skilled in this art from the following description wherein there are shown and described preferred embodiments of this invention, simply by way of illustration of the best modes suited for to carry out the invention. As it will be realized by those skilled in the art, the invention is capable of other different embodiments and its several details are capable of modifications in various obvious aspects all without departing from the scope of the subject application. Accordingly, the drawings and description will be regarded as illustrative in nature and not as restrictive.

BRIEF DESCRIPTION OF DRAWINGS

For a more complete understanding of the present invention and the advantages thereof, reference is now made to the following description taken in conjunction with the accompanying drawings, in which.

DETAILED DESCRIPTION OF THE INVENTION

The subject application is directed to a device and method for selective hyperthermic damage of target cells within the cells in a culture medium, and more specifically, to a method and device for selective hyperthermic damage of unwanted cells within a cell population with millimeter wave radiation.

As used herein the term "culture medium" is used to refer to a water-based medium used to maintain live cells.

As used herein the term "cultureware" is used to refer to a container used to hold cells placed in a culture medium.

As used herein the term "hyperthermic damage" is used to refer to damage due to overheating.

As used herein the term "irreversible damage" relates to a degree of damage after which the cells could not survive.

Figure 1:
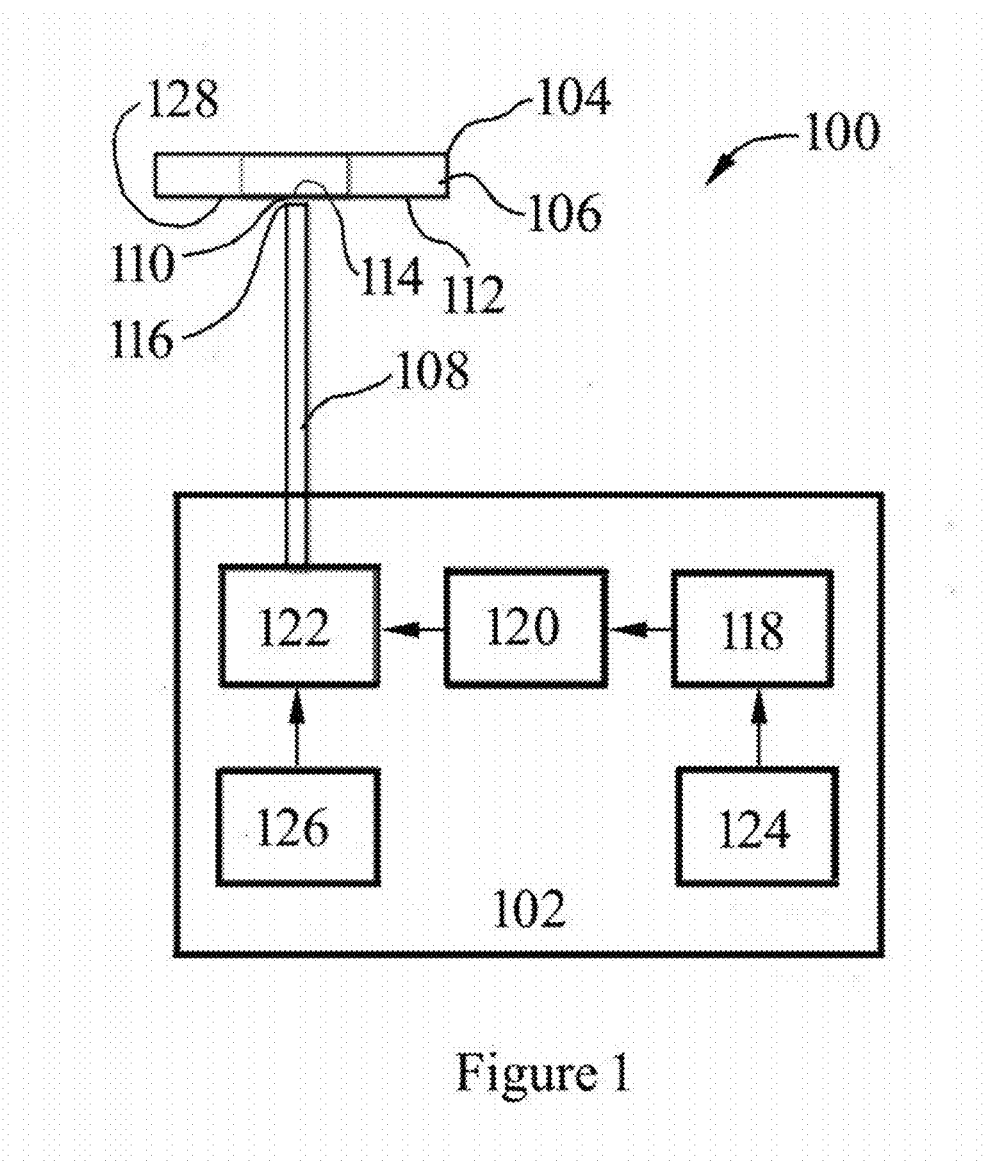
FIG. 1 is a block diagram of one embodiment of a device for selective hyperthermic damage of target cells in accordance with the subject application.

Turning now to FIG. 1, there is shown a block diagram of a preferred embodiment of a device 100 for selective hyperthermic damage of target cells in accordance with the subject application. As shown in FIG. 1, the device 100 includes a source 102 of millimeter wave radiation, an associated cell cultureware 104 having cells in a culture medium 106 placed therein, and a waveguide 108. The waveguide 108 is adapted for delivering the millimeter wave radiation to a predetermined spot 110 of an external surface 112 of the associated cell cultureware 104 to provide for exposing a predetermined region 114 of exposure of the cells in the cell culture medium 106 to the millimeter wave radiation. An end face 116 of the waveguide 108 is positioned in close proximity of the predetermined spot 110.

In a preferred embodiment, the source 102 operates in the W-band, which ranges from 75 to 110 GHz. In other preferred embodiments, a source that operates in the F, D, or G-band could be used as the source 102.

A skilled artisan will appreciate that the source 102 comprises, for example, and without limitation, a fixed frequency Gunn oscillator 118 (InP or GaN Gunn diode) that produces a stable output signal in the frequency range 75-110 GHz with a maximum power output of 65-100 mW, a passive variable attenuator 120 to control the radiation level, a narrow-band millimeter wave power amplifier 122 for increasing the millimeter wave radiation power to 250-400 mW or higher, power sources 124, 126 to feed the Gunn oscillator 118 and the millimeter wave power amplifier 122. As it will be appreciated by one skilled in the art, all above elements of the source 102 are commercially available. All basic elements of the source 102 may be placed in a separate enclosure (not shown).

In the embodiment illustrated in FIG. 1, the predetermined spot 110 of the external surface 112 is located on a bottom 128 of the associated cell cultureware 104. Thus the end face 116 of the waveguide 108 is positioned below the bottom 128 of the associated cell cultureware 106. However, in another embodiment, the predetermined spot 110 may be located on the top (lid) of the associated cell cultureware 104 (not shown in the drawing). Those skilled in the art will recognize that in such an embodiment, the position of the waveguide 108 is adapted accordingly.

The internal dimensions of the waveguide 108 or any portions thereof are determined by the frequency of millimeter wave radiation. For example, for millimeter wave radiation of 94 GHz the internal dimensions of the waveguide 108 are 2.540×1.270 mm (WR10), so the maximal diameter of the region 114 of exposure determined by the smallest dimension of the end face of the waveguide 108 is around 1 mm.

Figure 2:
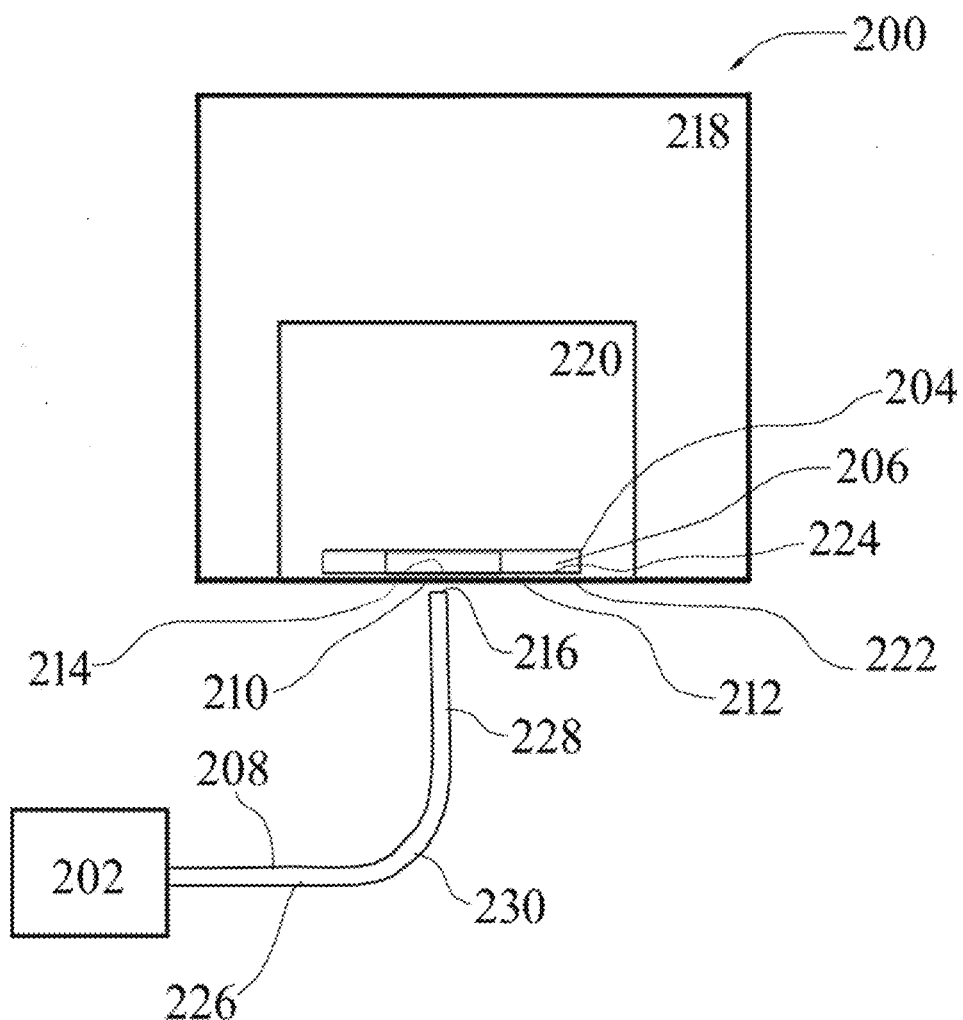
FIG. 2 is a block diagram of another embodiment of a device for selective hyperthermic damage of target cells in accordance with the subject application.

Turning now to FIG. 2, there is shown a block diagram of a preferred embodiment of a device 200 for selective hyperthermic damage of target cells in accordance with the subject application. As shown in FIG. 2, the device 200 includes a source 202 of millimeter wave radiation, an associated cell cultureware 204 having cells in a culture medium 206 placed therein, and a waveguide 208. The waveguide 208 is adapted for delivering the millimeter wave radiation to a predetermined spot 210 of an external surface 212 of the associated cell cultureware 204 to provide for exposing a predetermined region 214 of exposure of the cells in the culture medium 206 to the millimeter wave radiation. An end face 216 of the waveguide 208 is positioned in close proximity of the predetermined spot 210. Those skilled in the art will recognize that the source 202 may be analogous to the source 102 of the device 100.

In the embodiment of FIG. 2, the device 200 for selective hyperthermic damage of target cells further includes a visualizing module 218 adapted for visualizing the cells in the culture medium 206 placed in the associated cell cultureware 204. As will be appreciated by those skilled in the art, the visualizing module 218 comprises a microscope 220, wherein the associated cell cultureware 204 having cells in the culture medium 206 placed therein is positioned on a microscope stage 222. Those skilled in the art will further recognize that the microscope 220 is capable of being implemented, for example, and without limitation, as a fluorescent or a bright-field microscope, as an upright or an inverted microscope. In the embodiment of FIG. 2, the microscope 220 is implemented as an upright microscope. In this embodiment, the end face 216 of the waveguide 208 is positioned below a bottom 224 of the associated cell cultureware 204 having cells in a culture medium 206 placed therein, exposing thereby the predetermined region of exposure of the cells in the culture medium 206 located above the predetermined spot 210, to the millimeter wave radiation.

Further, in the embodiment of FIG. 2, the waveguide 208 comprises a first portion 226 positioned horizontally relative to the microscope stage 222 and a second portion 228 positioned upright relative to the microscope stage 222, wherein the second portion 228 is connected with the first portion 226 via a 90 degree E-plane waveguide bend 230. As will be understood by a skilled artisan, the portions of the waveguide 208 are commercially available, wherein the 90 degree E-plane waveguide bend 230 may be custom made.

Those skilled in the art will recognize that the visualizing module 218 may further comprise at least one of: a long working distance objective, a CCD camera or an infra-red camera for visualization on a monitor and image capture, and a motorized stage to hold and move the associated cell cultureware having cells in a culture medium placed therein (not shown in the drawings).

As will be further appreciated by those skilled in the art, the device for selective hyperthermic damage of target cells of the present invention may be implemented as a detachable device that can be easily attached to any standard microscope (up-right or inverted) with minor modifications of the microscope.

Referring now to operation of the device for selective hyperthermic damage of target cells 100 in accordance with the present invention, shown in FIG. 1, the operation of the device 100 commences by placing cells in the culture medium 106 within an associated cell cultureware 104. The cells in the culture medium 106 are kept sterile by a cultureware lid (not shown). Next, millimeter wave radiation from the source 102 is delivered via the waveguide 108 to the predetermined spot 110 of the external surface 112 of the associated cell cultureware 104 having cells in the culture medium 106 placed therein. The radiation power and exposure time of the millimeter wave radiation, and positional relationship of the end face 116 of the waveguide 108 and of the target cells are selected such as to expose the predetermined region 114 of exposure of the cells in the culture medium 106 to the millimeter wave radiation and provide selective hyperthermic damage to the target cells in the predetermined region 114. The predetermined region of exposure may have a diameter of less than 1.3 mm, preferably in the range of from about 0.25 mm to about 1.3 mm.

As will be understood by those skilled in the art, the millimeter wave radiation is absorbed in a very narrow layer (of about 0.4 mm or less) of the cells in the culture medium 106 and rapidly heats the narrow layer of the cells in the culture medium 106 comprising the unwanted cells, without heating the bulk of the cell cultureware 104. The cells locally heated by the millimeter wave radiation even for a short time are damaged, if necessary, irreversibly damaged and eliminated. Preferably, the exposure time is about 2-3 sec, wherein the target cells in the predetermined region 114 of exposure are heated to a temperature of about 58-60° C.

Referring now to operation of the device for selective hyperthermic damage of target cells 200 in accordance with the present invention, shown in FIG. 2, the operation of the device 200 commences by placing the cells in the culture medium 206 within the associated cell cultureware 204, the latter being placed on the microscope stage 222. The cells in the culture medium 206 are kept sterile by a cultureware lid (not shown). Next, the millimeter wave radiation, for example at a frequency of 94 GHz, from the source 202 is delivered via the first 226 and second 228 portions and the end face 216 of the waveguide 208 to the predetermined spot 210 of the external surface 212 of the associated cell cultureware 204 having cells in the culture medium 206 placed therein. The radiation power and exposure time of the millimeter wave radiation, and positional relationship of the end face 216 of the waveguide 208 and of the target cells are selected such as to expose the predetermined region 214 of exposure of the cells in the culture medium 206 to the millimeter wave radiation and provide selective hyperthermic damage to the target cells in the predetermined region 214 of exposure of the cells in the culture medium 206.

Specifically, in the embodiment of FIG. 2, the millimeter wave radiation passes through the first portion 226 of the waveguide 208 positioned horizontally relative to the microscope stage 222, and is then redirected by a 90 degree E-plane waveguide bend 230 mounted under the microscope stage 222 of an up-right microscope 220 to the second portion 228 positioned upright relative to the microscope stage 222. The cells that need to be selectively eliminated by irreversible hyperthermic damage may be visualized within the culture medium 206 by means of a visualizing module 218.

For example, in a bright-field mode the cells may be illuminated through a condenser (not shown) placed below the waveguide 208. The waveguide bend 230 may comprise an orifice of ~1 mm in diameter (not shown in the drawing) in the lower surface of the waveguide bend 230 to allow for the illumination light to reach the cells through the second portion 228 of the waveguide 208. The light scattered by the cells is collected by an objective (not shown in the drawing) focused on an internal surface of the cultureware 204. An image of the cells may be acquired by a CCD camera (not shown) capable of maintaining the video rate for real time imaging. The image or the real time stream may be digitized, displayed and stored by a computer (not shown). The microscope stage 222, if motorized, may be controlled by a joystick (not shown) and/or by the computer.

As known in the art, millimeter wave radiation is readily absorbed by water. For W-band (75 to 110 GHz) the penetration depth is about 0.4 mm in water based media. The major fraction of the power of W-band entering a water based medium decays exponentially within a layer 0.2-0.3 mm thick, i.e. the electromagnetic field energy is completely converted to heat in this narrow region.

Millimeter wave radiation can penetrate diamagnetic materials, such as glass and plastic, without power attenuation. When cells in the culture medium 206 within the cultureware 204 are exposed to the millimeter wave radiation guided to the glass or plastic external surface 212 of the bottom 224 of the cultureware 204, the millimeter wave radiation heats the culture medium and the cells near the external surface 212 of the cultureware 204, but not the external surface 212 itself. The temperature of the culture medium near the external surface 212 depends on the energy (amplitude and frequency) of millimeter wave radiation. The bottom portion of the culture medium (within a bottom layer of <0.4 mm thick) that is heated by millimeter wave radiation, moves up due to the convection phenomena so there is no damage to the neighboring cells around the region 214 of exposure. The cells in the region 214 of exposure are heated up to the temperature of about 60° C. that is much higher than the reported high-temperature survival threshold for all mammalian cells (48-50° C.).

The cells are irreversibly damaged in the region 214 of exposure when they are heated to about 60° C. within seconds. Heated (damaged) cells detach from bottom of the cultureware 204, become spherical and eventually are washed out when the media is changed.

Millimeter wave radiation is a form of non-ionizing radiation (meaning it can't directly break up atoms or molecules) that lies between common radio and infrared frequencies. So it is not thought to damage DNA, the way X and gamma rays do. Nevertheless, millimeter wave radiation can obviously cause heating effects, and can harm or kill at high energies. In accordance with the subject invention, in order to heat cells up to 60° C., about 100 mW of millimeter wave radiation power is applied to a region with diameter ~0.5-1 mm. A skilled artisan will appreciate that the millimeter wave radiation-mediated hyperthermic damage of the current invention is safe for an operator because the cell media completely absorbs all millimeter wave radiation power. Even if the equipment is accidentally turned on without the cell cultureware 204 on the stage 222, the millimeter wave radiation power is too low to harm the operator. Even 100 mW millimeter wave radiation fanning out from the end face 216 of the waveguide 208 will expose the operator to much less than a maximum permissible exposure for uncontrolled environments of 10 $Wm^{-2}$ (IEEE, 2005).

Further, to exclude a power-on without the cell cultureware 204 placed over the end face 216 of the waveguide 208 a simple millimeter wave radiation detector may be placed near the microscope objective (not shown in the drawings). The millimeter wave radiation detector may be arranged to "power off" the Gunn oscillator of the source 202, if high millimeter wave radiation intensity is detected. One skilled in the art will recognize that such detectors are well known in the art, and any such millimeter wave radiation detector is capable of being suitably included in the device.

Below are Examples of using the method for selective hyperthermic damage of target cells in accordance with the present invention.

Calibration

Figure 3:
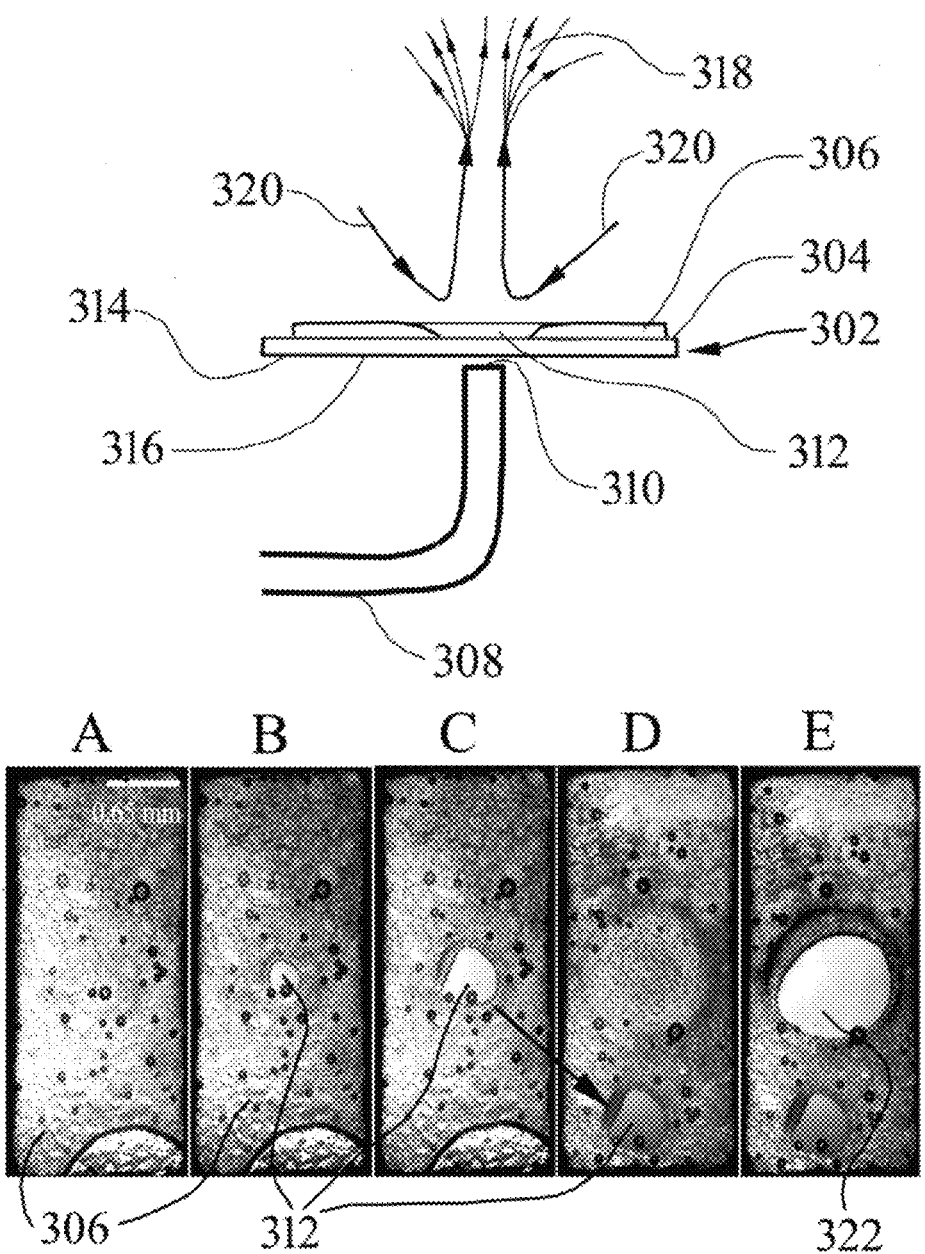
FIG. 3 illustrates a calibration process in accordance with the subject application.

Prior to operation, the device of the present invention is preferably calibrated. The calibration procedure is illustrated in FIG. 3 and will be described with reference to the embodiment shown in FIG. 2, though it should be understood that a similar procedure may be performed for the embodiment of FIG. 1. The calibration procedure is performed to ensure that the millimeter wave radiation level is high enough to heat the cells in the region of exposure to the desired temperatures (58-60° C.).

The calibration procedure starts by preparing a calibration plate 302 that is similar to the cultureware 204. The internal surface 304 of the calibration plate 302 is preferably coated with a thin film (about 10 μm thick) of long-chain alcohol (LCA) with a known melting point temperature. In a specific embodiment, the internal surface 304 is coated with a thin film 306 of 1-Octadecanol (1-OD) that has a melting point temperature of 58° C. Image A in FIG. 3 shows an unmelted 1-OD microfilm.

Next, a millimeter wave radiation at a frequency in the range of 75-110 GHz with the time of exposure of about 2-3 seconds is applied to the coated calibration plate 302 via a waveguide 308 with an end face 310 positioned below the calibration plate 302. This leads to melting of an area 312 in the 1-OD microfilm 306. The melting process may be visualized with phase contrast microscopy: image A of FIG. 3 shows the 1-OD microfilm 306 before application of the millimeter wave radiation, image B was acquired about 1 second after application of the millimeter wave radiation when the melted area 312 has started to appear, image C was acquired several seconds after application of the millimeter wave radiation when the melted area 312 has stopped extending and reached the size of approximately 0.3 mm.

As will be appreciated by one skilled in the art, by adjusting exposure parameters such as the radiation power and exposure time of the millimeter wave radiation, and positional relationship of the end face 310 of the waveguide 308 and of the calibration plate 302, a bigger or smaller melting area 312 may be attained. Images D-E of FIG. 3 illustrate obtaining a bigger melted area 322 of approximately 0.7 mm in diameter by increasing the power of the millimeter wave radiation (the arrow between images C and D indicates that the 1-OD microfilm 306 was moved to melt the bigger area 322 at a different position than the position of the smaller area 312). In a specific embodiment, a 2× air objective lens with a large working distance and a small numerical aperture (not shown in the drawing) was used to observe the microfilm 306.

Lower millimeter wave radiation power results in a smaller diameter of the melting area 312. Thus, smaller melted microfilm area 312 may be obtained when the source 202 (FIG. 2) of millimeter wave radiation is adjusted to a lower power via a variable attenuator (not shown) and/or when the end face 310 of the waveguide 308 is positioned farther from the external surface 314 of the calibration plate bottom 316. For precise single cell hyperthermic damage the diameter of the region of exposure may be decreased to 0.25 mm or less. The maximal size of the melting area 312 (about 1 mm in diameter) is determined by the wavelength of millimeter wave radiation in the W-band. Thus, the equipment can be calibrated to ablate cells in areas with different diameters.

For best results, the calibration procedure is preferably performed under conditions very similar to the conditions at which the cells would be treated: the calibration plate 302 with the microfilm containing the same volume of the same culture medium as the cell cultureware 204 (FIG. 2) with the cells placed therein. The LCA film 306 melts when the culture medium closely adjacent to the film 306 is heated via application of the millimeter wave radiation. The heated culture medium 318 moves upward creating a convectional flow 320; therefore the film adjacent to the region of exposure is not heated (FIG. 3). As it would be appreciated by one skilled in the art, in the absence of the culture medium in the calibration plate 302, no melting of the LCA microfilm is observed (data not shown). This is consistent with the fact that, as known in the art, absorption of millimeter wave radiation by LCA, higher alkanes or oils is negligible.

Thus LCA/alcane microfilms may serve as local sensors of the temperature in a narrow layer (~10-15 μm thick) of cell culture medium at the glass/plastic bottom of the calibration plate 302. The LCA microfilm may also be formed directly in the cultureware 204 (FIG. 2) having cells in a culture medium 206 placed therein to allow performing the calibration procedure in the same plate, in close proximity to the cells.

After the millimeter wave radiation power is adjusted, the hyperthermic damage process is started to expose the unwanted cells and/or cell colonies to millimeter wave radiation. The hyperthermic damage results become visible in a few hours after the treatment. This time interval is shorter for higher temperatures or high millimeter wave radiation powers. The cells exposed to lethal millimeter wave radiation power detach from the substrate and can be easily washed out by simple media change. If some unwanted cells are still found after the first treatment, the procedure can be repeated to completely eliminate them.

Effect of 94 GHz Irradiation (Heating to 60° C.) on U2OS Cells Expressing GFP-Tubulin.

Figure 4:
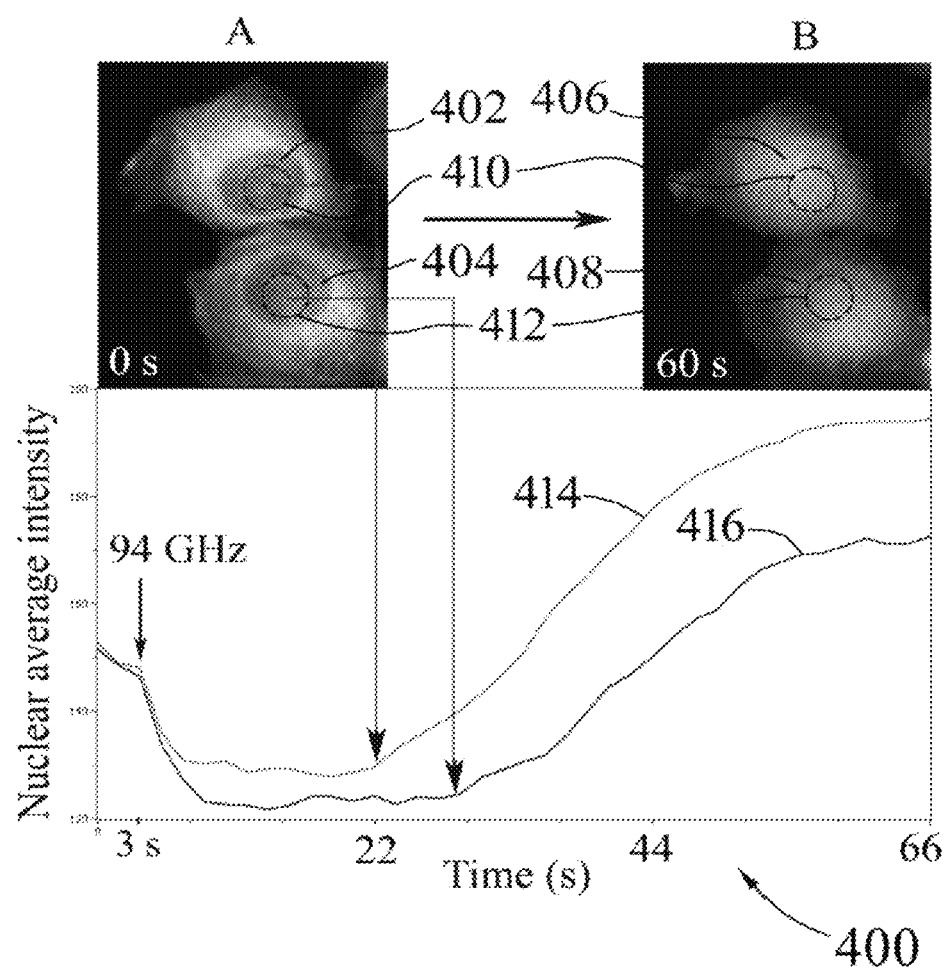
FIG. 4 shows the effect of 94 GHz irradiation (heating to 60° C.) on U2OS cells expressing fusion protein of α-tubulin and green fluorescent protein (GFP-tubulin).

As known in the art, mammalian cells do not survive even a short-term exposure to 60° C. To better define the time of irradiation required to irreversibly damage the cells in the region of exposure, the cells expressing GFP-tubulin were exposed to 94 GHz millimeter wave radiation. The power of millimeter wave radiation was adjusted to melt the 1-OD microfilm 306 (FIG. 3) with melting temperature ~58° C. in 10-15 seconds. Normally GFP-tubulin is excluded from the cell nucleus 402, 404 (FIG. 4, panel A). It was observed, however, that after about 20 seconds of millimeter wave radiation GFP-tubulin started entering the cell nucleus and then the nuclear GFP-tubulin concentration equilibrated with the cytoplasm 406, 408 (FIG. 4, panel B) indicating that the nuclear envelope was compromised. This shows that a sudden disruption of the nuclear envelope permeability happens when cells are rapidly heated to 58-60° C. as the proteins that are normally excluded from the nucleus (like GFP-tubulin) enter it.

The graph 400 in FIG. 4 shows the fluorescence intensity of the regions of interest (dotted circles 410, 412) inside the nuclei of two cells as a function of time. The curve 414 on the graph shows the average intensity in the circle 410 on panels A-B. The curve 416 on the graph shows the average fluorescence intensity in the circle 412 on panels A-B. The sharp drop in the GFP fluorescence after application of 94 GHz millimeter wave radiation (arrow at 3 seconds) is attributed to a drop in the GFP quantum yield when the temperature rises. The arrowheads mark the beginning of GFP-tubulin entry into the nucleus that indicates damage in the barrier function of the nuclear envelops.

It was also observed that cells exposed to the high temperatures demonstrate reversible membrane bleb formation (not shown).

Effect of 94 GHz Millimeter Wave Radiation on the Cells 6 Hours after Exposure.

Figure 5A:
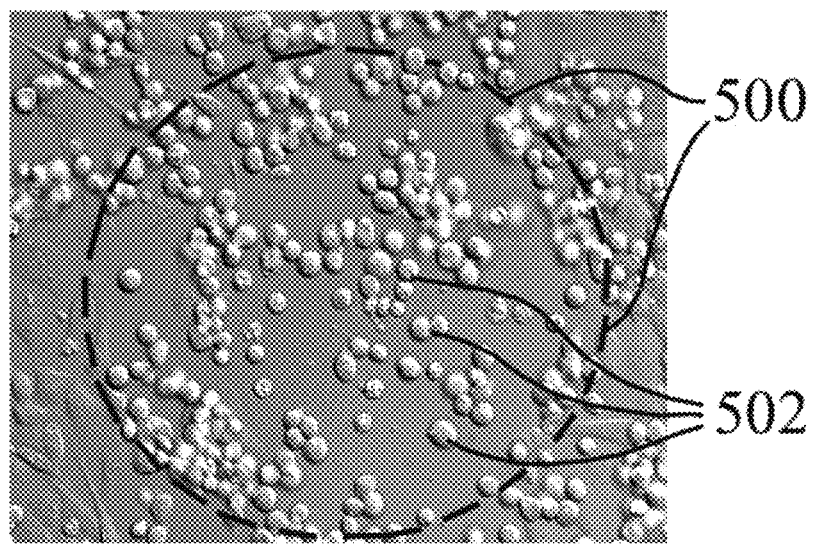
FIG. 5a shows the effect of 94 GHz millimeter wave radiation on the cells 6 hours after exposure.

FIG. 5a shows a follow up observation of a region 500 of exposure. The follow up observation of the region 500 was performed with a 20× objective using differential interference contrast (DIC). The observation of the region 500 performed 6 hours after the exposure to the millimeter wave radiation revealed that the cells 502 in the region 500 of exposure detach from the well bottom and become spherical.

Confluent Cell Culture Exposed to 94 GHz Millimeter Wave Radiation and Washed Out 9 Hours Later to Remove Dead or Detached Cells.

Figure 5B:
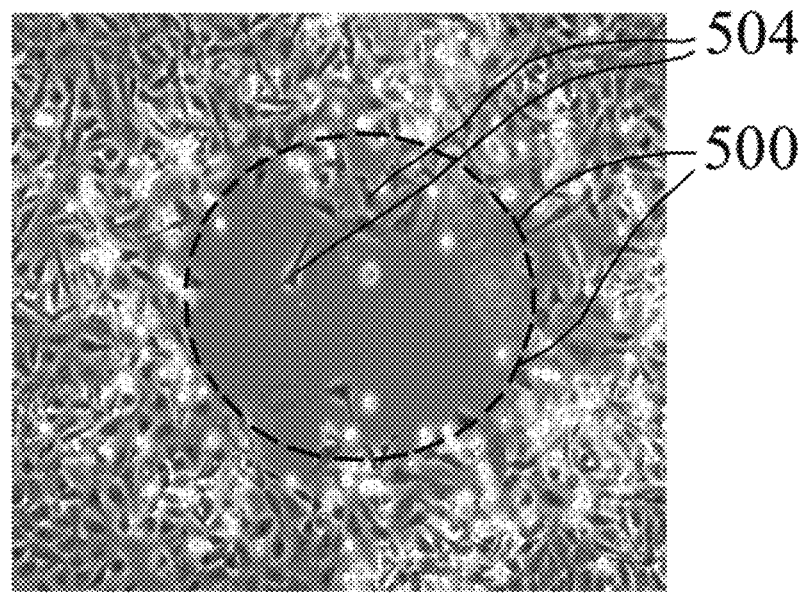
FIG. 5b illustrates the confluent cell culture exposed to 94 GHz millimeter wave radiation and washed out 9 hours later to remove dead or detached cells.

FIG. 5b shows a further follow up observation of the region 500 of exposure. The next follow up observation of the region 500 was performed with a 20× objective with a 20× objective using phase contrast. The observation performed 9 hours after the exposure to the millimeter wave radiation and after washing out the cells with a culture medium showed that washing out the cells removes the spherical cells and leaves a clear (cell-free) internal surface surrounded by the confluent cell culture. The exposure parameters adjusted to obtain a desired diameter of the melting area in the calibration procedure described herein were used to produce the same desired diameter of the region of exposure of the cells in the culture medium where the cells were totally eliminated. As seen from FIG. 5b, the neighboring cells 504 that grow at the edge of the region 500 of exposure were not damaged. They continued to grow and actively migrated to the now empty area (region 500).

Thus the method of the current invention allows for eliminating of unwanted cells selectively even within confluent cell culture. The elimination process may be repeated several times before the unwanted cells are completely removed.

Applying Millimeter Wave Radiation to Two Closely Adjacent Regions.

Figure 6:
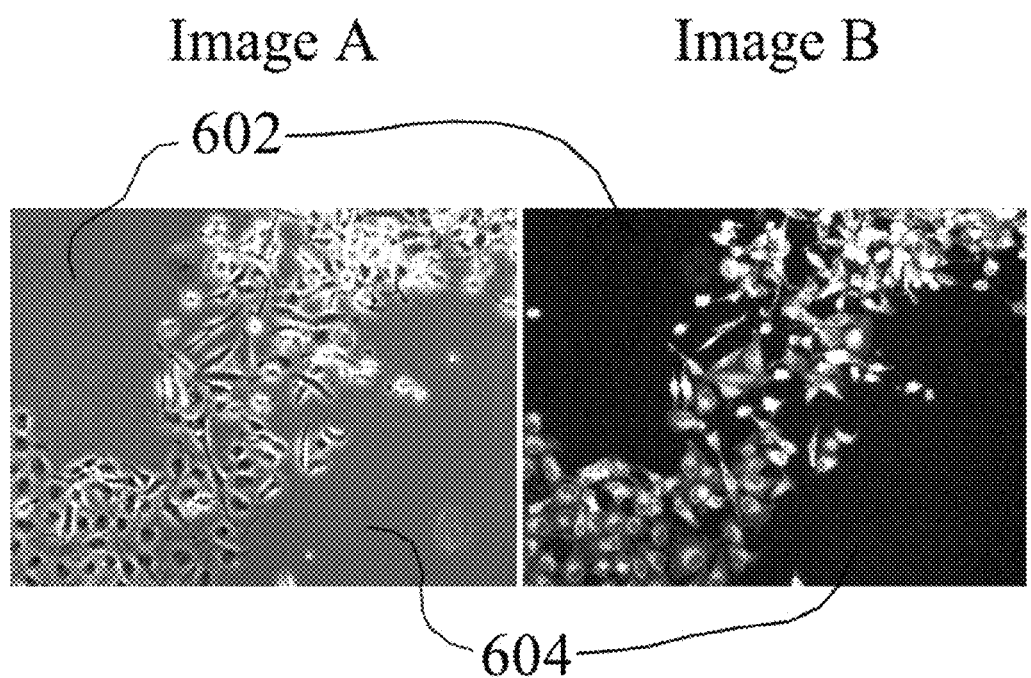
FIG. 6 illustrates applying millimeter wave radiation to two closely adjacent regions.

FIG. 6 illustrates applying of millimeter wave radiation to two closely adjacent regions 602, 604 of exposure. As seen in FIG. 6, the cells in these regions 602, 604 are completely eliminated via millimeter wave radiation irradiation. The two regions 602, 604 are in a very close proximity to each other (~250 μm). However, the cells between the regions 602, 604 survived the treatment and continue to grow. Image A is acquired using bright field phase contrast, image B depicts GFP fluorescence as the cells are expressing GFP-tubulin.

The method of the invention can be applied to cell suspensions as well. In this case prior to applying millimeter wave radiation it is necessarily to wait until all the cells settle at the cultureware bottom and then mark the desired regions where the cells should survive. The operator (or software) can drive the microscope stage to expose cells in unmarked regions to millimeter wave radiation that heat them to 60° C. The heated cells will eventually die but the cells in the regions that were not exposed to millimeter wave radiation will survive and continue to grow.

Sectioning of the Cell Culture by Millimeter Wave Radiation.

Figure 7:
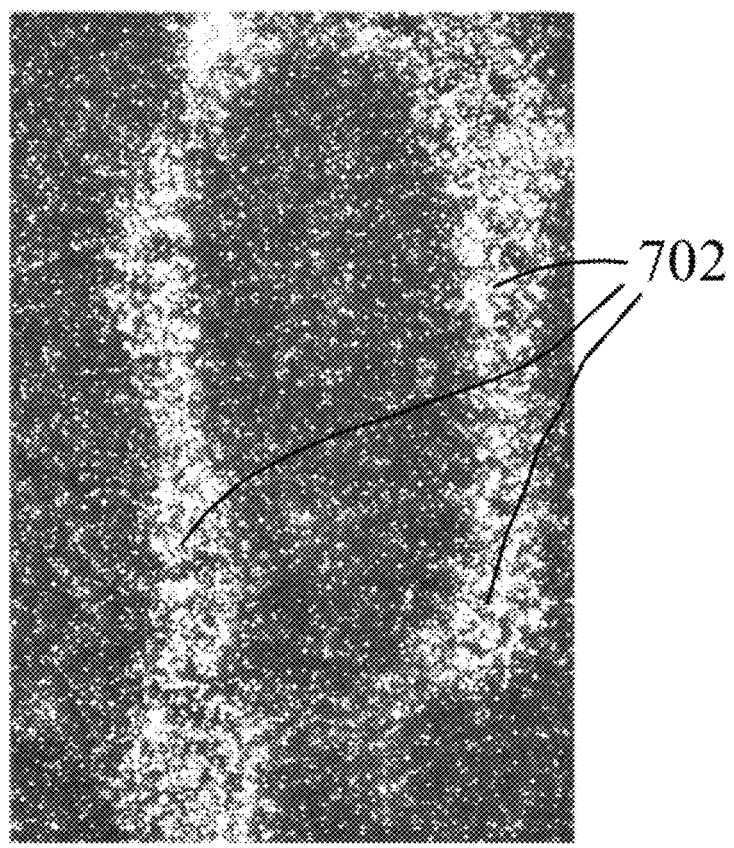
FIG. 7 demonstrates sectioning of the cell culture by millimeter wave radiation.

The method of the invention may be used for making sections in a confluent or semi-confluent cell culture. This may be done manually or with the use of a software-driven motorized microscope stage, provided that the stage is moved slow enough to expose the cells to lethal millimeter wave radiation dose. The width of the sectioning line may be 1 mm or less. The trajectory 702 of the sectioning line becomes visible even under low magnification bright-field objective (2×) because exposed cells round up and are observed as a light line (spherical dead cells) against surrounding live culture (flat and dark) as seen on FIG. 7 that shows a bright field image of a confluent cell culture under 2× magnification. The light P-like line is a trajectory of the region of exposure in the confluent cell culture (9 hours after treatment).

The following examples clarify possible applications of the described method and device for selective hyperthermic damage of target cells.

Example 1

Selection of Desirable Single Cell Clones in Biotechnology Applications

In some applications cells are seeded at low density to isolate single cell colonies for cell line development. Usually several cells are placed per well in a cell culture plate (manually via delimited dilution or automatically by flow cytometry sorting) to allow formation of separated colonies. If cells are single cell sorted or seeded to get single colonies, many cell lines show poor survival of single cell clones and slow initial outgrow rate. Better cell survival and growth rate are achieved with placement of several or more cells per well as they condition the culture medium. As the end result, only one single-cell colony that possesses some useful properties (fluorescent protein knock-in, the knock-out of a surface antigen, etc.) needs to be isolated. Therefore all unwanted colonies that helped the desired colony to survive should be eliminated. Overheating by millimeter wave radiation offers a safe and effective way to do so. The elimination is based on a feature distinguishing the desired cells that are kept alive (a specific morphology, a fluorescent signal coming from genetically engineered fluorescent proteins, a surface marker that could be revealed by fluorescently-labeled antibodies, etc.). The method of the current invention allows eliminating all unwanted colonies and keeping alive only a specific single cell colony that exhibits a desired phenotype.

Example 2

Generation of Tumor Cell Cultures Originated from Cancer Patient Tumor Biopsy.

In another application, the tumor biopsies are collected from cancer patients to establish the primary human tumor cell cultures. However, the biopsy samples are extremely heterogeneous due to the presence of other tissue cells like fibroblasts. In most cases these cells grow fast in cultures and easily can overgrow the desired tumor cells. The disclosed device may be used to distinguish the unwanted contaminating cells (via differences in morphology or using fluorescent labels) and to eliminate (ablate) them without damaging the neighboring tumor cells. The millimeter wave radiation hyperthermia ablation of fast-growing primary non-tumor cells (fibroblasts or others) may provide superior conditions for the growth of the desired tumor cells and may allow establishing more homogenous culture of patient tumor cells.

Example 3

Coculture Micropatterning of Primary Cells.

Primary cells are thought to be the best test models of human organs and tissues for drug discovery and ADME/Tox profiling. The problem is that they are viable only for a few days and/or their organ-specific functions rapidly decline under conventional culture conditions. Coculture micropatterning of primary cells (e.g. hepatocytes) and supporting cells (e.g. fibroblasts) creates primary cell clustering known to extend the lifespan of primary cells in culture and improve their organ-specific functions. The millimeter wave radiation hyperthermia ablation may be used to create micropatterned voids in the supporting culture.

Then the voids can be seeded with the primary cells to create micropatterned clusters surrounded by the supporting cells. This approach provides a simple and inexpensive way to fabricate micropatterned cocultures.

Example 4

Induced Pluripotent Stem (iPS) Cells and Embryonic Stem (ES) Cells Therapies.

Another application involves the use of induced pluripotent stem (iPS) cells to treat numerous human diseases. The iPS cells are capable of differentiation in a way that is very similar to embryonic stem (ES) cells which can grow into fully differentiated tissues. iPS cells and ES cells express the same cell surface antigenic markers. Both cell types might be used to generate different types of tissues via differentiation processes. Then the differentiated tissues (cardiomyocytes, hepatocytes, neurons, etc.) can be used in transplantation. However, differentiation of both iPS and ES cells usually yields mixed cell population i.e. both differentiated and undifferentiated cells. The transplantation of undifferentiated cells in patients might lead to tumor formation. Thus, the therapeutic use of tissues derived from both iPS and ES cells is possible only after the purification i.e. complete elimination of undifferentiated stem cells. The method described herein allows purifying the mixed cell culture by selective elimination of practically all undifferentiated stem cells or cells that spontaneously differentiated to another cell types. The purified tissue could be implanted to the patients.

Example 5

Wound-Healing Assay.

The wound-healing assay is simple, inexpensive, and one of the earliest developed methods to study directional cell migration in vitro. This method mimics cell migration during wound healing in vivo. The basic steps involve creating a "wound" in a cell monolayer, capturing the images at the beginning and at regular intervals during cell migration to close the wound, and comparing the images to quantify the migration rate of the cells. It is particularly suitable for studies of the effects of cell-matrix and cell-cell interactions on cell migration. Usually the wound is created my mechanical scratch of cell monolayer, via application of biocompatible hydrogel to bottom that creates a circular area across which cells may migrate following gel removal or via placement of special silicone inserts to the cell culture surface before cell seeding (when the insert is removed it creates well defined empty regions with no cells). The disclosed device could be used to make precise circular holes in cell monolayer without creating any mechanical or chemical disturbance of the surrounding cells. The high temperature (60° C. or more) will induce the denaturation of all extracellular matrix proteins that were produced by growing cells. So the migration cells must produce them anew.

Example 6

Hyperthermia Therapy Studies

Hyperthermia therapy is a type of medical treatment in which body tissue is exposed to slightly higher temperatures to damage and kill cancer cells or to make cancer cells more sensitive to the effects of radiation and certain anti-cancer drugs. Hyperthermia may kill or weaken tumor cells, and is controlled to limit effects on healthy cells. In many cases hyperthermia is performed via application of radiofrequency (RF) waves to ablate tumor tissues. Cancerous cells are not inherently more susceptible to the effects of heat. When compared in in vitro studies, normal cells and cancer cells show the same responses to heat. However, the cancer cells might be selectively sensitized to hyperthermia treatment with special drugs. The disclosed device and method may provide an experimental tool for high-content screening of compounds that selectively sensitize cancer cells to hyperthermia therapy. For example, the cancer cells might be mixed with normal cells to yield a mixed cell culture. The tested compound is added to the culture media and after a pre-incubation period the millimeter wave radiation is applied to the culture to increase the temperature to sub-lethal level (below 48° C.). If the tested compound makes cancer cells significantly less able to tolerate the added heat stress than the healthy cells, the millimeter wave radiation application will lead to cancer cells dying but normal cells surviving. The found hit compounds could be used to increase the effect of radiofrequency ablation in cancer patients.

Example 7

Generation of Single Cell Clones After DNA, mRNA or Protein Microinjection in Adherent Cells.

Novel genetically modified cell lines could be developed by various molecular biology methods for genome editing. An essential step in the process is the delivery of DNA, mRNA or protein (e.g. site specific nucleases) inside the parental cells. Microinjection is the most direct, predictable and effective way for the delivery but practically it is impossible to isolate injected (and then genetically modified) cells from the majority of the unmodified ones. The disclosed device may be used to visualize unmodified cells (via bright-field microscopy or fluorescent labels) and eliminate (ablate) them without damaging the desired, genetically modified cells.

The foregoing description of preferred embodiments of the subject application has been presented for purposes of illustration and description. It is not intended to be exhaustive or to limit the subject application to the precise form disclosed. Obvious modifications or variations are possible in light of the above teachings. The embodiment was chosen and described to provide the best illustration of the principles of the subject application and its practical application to thereby enable one of ordinary skill in the art to use the subject application in various embodiments and with various modifications as are suited to the particular use contemplated. All such modifications and variations are within the scope of the subject application as determined by the appended claims when interpreted in accordance with the breadth to which they are fairly, legally and equitably entitled.

What is claimed:

1. A device for selective hyperthermic damage of target cells, comprising:
   a source of millimeter wave radiation; and
   a waveguide adapted for delivering the millimeter wave radiation to a predetermined spot of an external surface of an associated cell cultureware having cells in a culture medium placed therein, to provide for exposing a predetermined region of exposure of the cells in the culture medium to the millimeter wave radiation;
   wherein an end face of the waveguide is positioned in close proximity of the predetermined spot, and
   wherein radiation power and exposure time of the millimeter wave radiation, and positional relationship of the end face of the waveguide and the target cells are selected such as to provide selective hyperthermic damage to the target cells in the predetermined region of exposure of the cells in the culture medium,
   wherein the millimeter wave radiation is in a frequency band selected from W-band, F-band, D-band, or G-band, and has a water penetration depth of about 0.4 mm or less.

2. The device according to claim 1, further comprising a visualizing module adapted for visualizing the cells in the culture medium placed in the associated cell cultureware.

3. The device according to claim 2, wherein the visualizing module comprises a microscope, wherein the associated cell cultureware having the cells in the culture medium placed therein is positioned on a microscope stage.

4. The device according to claim 3, wherein the microscope is motorized.

5. The device according to claim 3, wherein the microscope is a fluorescent or a bright-field microscope.

6. The device according to claim 3, wherein the microscope is an upright microscope, and wherein the end face of the waveguide is positioned below a bottom of the associated cell cultureware having the cells in the culture medium placed therein, exposing thereby the predetermined region of exposure of the cells in the culture medium located above the predetermined spot, to the millimeter wave radiation.

7. The device according to claim 6, wherein the waveguide comprises a first portion positioned horizontally relative to the microscope stage and a second portion positioned upright relative to the microscope stage, wherein the second portion is connected with the first portion via a 90 degree E-plane waveguide bend.

8. The device according to claim 3, wherein the visualizing module further comprises at least one of: a long working distance objective, a CCD camera for image capture, an infra-red camera for visualization on a monitor and a motorized stage to hold and move the associated cell cultureware having the cells in the culture medium placed therein.

* * * * *